United States Patent [19]

Ferrell

[11] 4,307,339
[45] Dec. 22, 1981

[54] PARTICLE COUNTER

[76] Inventor: Michael W. Ferrell, 123 Edgemont Rd., Scarsdale, N.Y. 10583

[21] Appl. No.: 101,839

[22] Filed: Dec. 10, 1979

[51] Int. Cl.³ .............................................. G01N 27/00
[52] U.S. Cl. ............................ 324/71 CP; 73/432 PS
[58] Field of Search .............. 324/71 CP; 73/432 PS; 235/92 PS

[56] References Cited

U.S. PATENT DOCUMENTS

| | | | |
|---|---|---|---|
| 3,238,452 | 3/1966 | Schmitt et al. | 324/71 CP |
| 3,763,428 | 10/1973 | Preist | 324/71 CP |
| 3,815,024 | 6/1974 | Bean | 324/71 CP |
| 3,882,385 | 5/1975 | Coulter | 324/71 CP |

*Primary Examiner*—Michael J. Tokar

[57] ABSTRACT

A particle counter for determining the size and count of particulate substances suspended in an electrolytic solution includes a tube having an inlet hole for the passage of the solution therethrough, a pump connected to the tube for drawing the solution into the tube through the inlet hole, a pair of electrodes arranged on either side of the inlet hole in the flow path of the solution, and voltage monitoring apparatus for sensing fluctuations of voltage across the electrodes as particles pass through the inlet. A screen having precision size openings is disposed about the tube in the flow path of the solution prior to passage through the inlet hole for screening particles above a pre-determined size prior to reaching the inlet hole.

6 Claims, 2 Drawing Figures

PARTICLE COUNTER

BACKGROUND OF THE INVENTION

Many applications require accurate sizing and counting of particles, powders, granular substances, aerosols, blood cells, or any material that has a component which is made up of discrete parts of well defined dimensions. Hereafter, such materials will be referred to as particulates or particulate matter.

One known apparatus for sizing and counting of particulates is manufactured by Coulter Electronics, Hialeah, Fla. A particle counter of this type operates with an electrolyte bath and includes a constant current source, a voltmeter, memory circuits, a mechanical stirrer, electrodes, and a tube having a small inlet hole therein for the passage of fluid. The tube is immersed in the electrodes and a vacuum pump is connected to the upper end of the tube to draw fluid. One of the electrolytes is positioned in the tube, and the other is positioned in the electrolyte bath, such that the inlet hole lies between the electrodes in the fluid flow path.

The substance to be sized and counted is first immersed in a conductive electrolyte, such as aqueous NaCl, in order to make a very dilute suspension. A constant current is supplied between the electrodes, and the mechanical stirrer maintains the particulate matter well dispersed. The vacuum source draws the suspension through the small inlet hole into the tube. As a particle in the suspension passes through the inlet hole, a voltage pulse is generated that is directly proportional to the volume of the particle. The number of pulses accumulated represents the particle count, and the magnitude of each pulse or count is measured. In order that the measurements have an absolute (as opposed to relative) meaning, the pulses are calibrated against materials whose sizes have been determined by other methods, such as microscopic analysis. Thus, only through this two step process can both the actual sizes of the particles, as well as the count, be determined.

While the foregoing apparatus and method may be used to measure with some degree of accuracy the particle size and count, there are four basic problems associated with its usage: (a) the calibration techniques used do not always assure accurate calculation of particle size, and therefore the size distribution of particles may be erroneous; (b) materials used to calibrate the process against size determinations by other methods are not always readily available, are expensive, and often not well suited for such purpose; (c) the volume-proportional response of the system is only claimed to be a valid assumption for particulate matter having a maximum linear dimension of from 2 percent to 40 percent of the maximum cross sectional linear dimension of the inlet hole; and (d) particulates having a linear dimension larger than the minimum cross sectional linear dimension of the inlet hole tend to plug the inlet hole, sometimes resulting in costly damage, and in any case rendering the analysis inaccurate.

In present analysis work, the first two problems set forth above were considered inherent, and unless alleviated through considerable time and expense were merely tolerated. The remaining two problems are usually dealt with by extensive sample preparation to separate the sample into ranges of particulates of suitable dimensions for given inlet hole sizes so that by selection of an appropriate inlet hole size for a given size range, accurate measurement results can be obtained without the danger of clogging the inlet.

Usually such sample preparation falls into one of two broad categories: fluid calssification or mechanical classification. Fluid classification would include such devices and processes as elutriators against gravity and fluid classifiers against the centrifugal field. Mechanical classification would include such processes as wet or dry sieving. Unfortunately, either general method may lead to unrepresentative sample splitting because of large surface areas present, for example of the sieve, onto which fine particulates adhere. Since the prepared sample is no longer characteristic of the particulate material from which the sample was taken, a characteristic measurement cannot be performed.

SUMMARY OF THE INVENTION

The present invention is an improvement in the apparatus and process described above. More specifically, in apparatus such as the Coulter particle counter described above a filter of predetermined dimensions is placed between the electrodes and in the flow path of the dilute electrolytic particulate suspension to effect a pre-screening of particles which are in solution. This novel configuration allows the user to simultaneously prepare, split, and analyze a sample of particulates, or to screen out particles which are of dimensions too large for a selected tube inlet opening. The dilute electrolytic suspension of particles is drawn through the mechanical filter, which has a relatively large cross section so as not to impede the flow of fluid toward the inlet except to block out the undesired larger particles. Once the solution, now containing only particles of the desired size, passes through the screen or filter, it continues through the inlet opening, which constitutes an electrical sensing zone, for the purpose of obtaining a particle size analysis. The use of a precision made screen eliminates the need for a reference material for absolute comparisons, and moreover a screen apparatus according to the present invention will not disturb the electric field between the electrodes, and will not, excepting the elimination of the larger particles, otherwise affect the sample of particulates in suspension. Such a screen is hereinafter referred to as a passive screen.

DETAILED DESCRIPTION OF A PREFERRED EMBODIMENT

Figure 1:
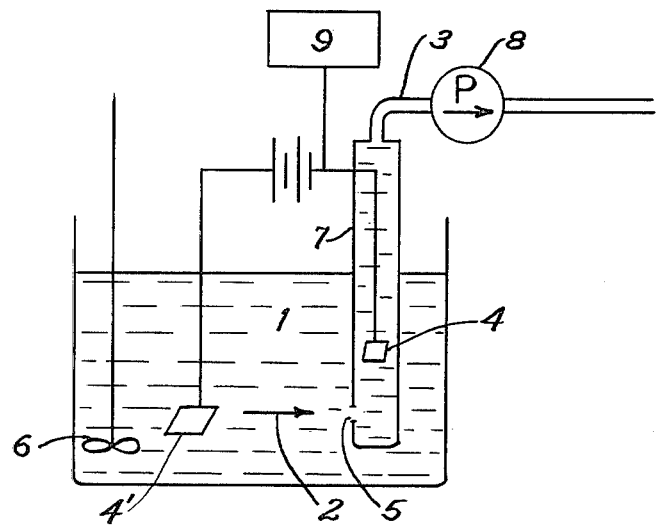
FIG. 1 is a schematic drawing of a particle counter of the type previously used prior to the present invention.

Referring to the drawings, a particle counter according to the invention is used with an electrolytic solution 1, into which the material to be analyzed has been introduced and dispersed. A mechanical stirrer 6 circulates the solution to maintain the particles in suspension and relatively dispersed.

In FIG. 1, apparatus of a known type is illustrated schematically. A tube 7 is immersed in the solution 1, and connected to an outlet line 3. The tube 7 contains an inlet hole 5 of a desired size for the range of particles to be measured. A typical size of such inlet hole is approximately 0.1 mm. A pump 8 is placed in the outlet line 3 to draw fluid through the inlet 5 and out through the top of the tube 7.

A pair of electrodes is also placed into the suspension. One electrode 4 is disposed in the tube itself, while the other electrode 4' is placed in the electrolytic solution 1, such that the inlet 5 lies in the flow path 2 of the solution 1 between the electrodes 4, 4'. Monitoring apparatus, itself known and generally designated as 9, sense and record the particle count (frequency of pulses) and the respective pulse sizes of the particles as they pass through the inlet 5.

Figure 2:
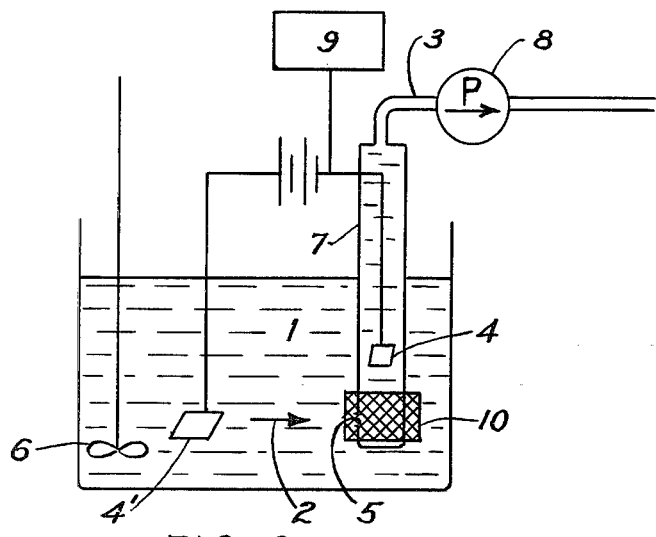
FIG. 2 is a schematic drawing of a particle counter having a particulate screen in accordance with the invention.

Referring to FIG. 2, in accordance with the present invention apparatus for measuring and counting particles includes a screen or filter 10 which is disposed in the flow path 2 between the electrolytic solution 1 and the inlet 5. As illustrated, the screen is a fine mesh precision screen of predetermined opening size for permitting only particles below a desired size from reaching the inlet 5. The screen 10 may be formed integrally on the tube itself, or alternatively may be supported by the walls of the bath or externally. Preferably, the screen 10 is spaced apart from the tube itself to permit the solution to circulate within the screen prior to entering the inlet 5. Thus, the flow area immediately prior to the inlet 5 is maintained relatively large such that larger particles which may lodge against the screen do not block the flow into the inlet 5.

The screen 10 may be formulated of any suitable material, and may be metallic since being stationary, it will not affect the reference electric field, i.e. is a passive screen.

Thus, in accordance with the invention, the four shortcomings with the prior art devices and methods are alleviated. Since the screen material is of precise and uniform hole size, the overall sizing process can be given absolute meaning by comparing the largest particulates sized by the electrical sensing zone method to the hole size of the screen material. At the same time, undesireably large particles are eliminated from the electrolyte flow path 2 prior to reaching the inlet. Thus the inlet opening 5 can be chosen to give representative fluctuations in voltage by selecting smaller opening sizes for smaller size measurements without the danger of clogging from larger particles, and without the need for expensive, time consuming, and unreliable particle separation techniques.

In a further refinement of the invention, an entire suspension of particles of varying sizes may be analyzed in a continuous process by utilyzing several or a series of apparatus of the type described herein. This embodiment has not been specifically illustrated since it should be readily apparent from the discussion which follows. Referring to FIG. 2, an initial particle suspension to be analyzed is placed in an electrolyte solution 1 in a first electrolyte bath. The screen 10 is selected to allow through the largest size particle which it is desired to measure. Accordingly, size and count measurements for large particles are obtained by selecting an appropriate size inlet 5. As described earlier, however, such measurements may not be accurate for smaller particles. The output of the pump 8, however, is directed into a second bath container (not shown), where the suspension will flow essentially with the same particle population (less the very large particles eliminated by the filter 10).

The process is repeated in the second container but with a smaller mesh screen, to obtain size and counts for a smaller particle range. The process may continue in this manner, in each case for a smaller range of the remaining particles.

Thus, the present invention provides the advantage of obtaining absolute sizing analysis in one initial step, and minimizes rigid surface areas on which particulates can accumulate. Therefore, the present invention provides an improved method and apparatus for measuring particle size and count, which is easy to use and more accurate than known devices.

The invention has been described and illustrated with reference to certain preferred embodiments thereof. Variations and modifications will be apparant to persons skilled in the art without departing from the inventive principles disclosed herein. All such variations and modifications are intended to be within the scope of the present invention as defined in the following claims.

I claim:

1. In a particle counter apparatus for determining the size and count of particulate substances suspended in an electrolytic solution including a tube having an inlet hole for the passage of the solution therethrough, a pump connected to the tube for drawing the solution containing the particulates into the tube through the inlet hole, a pair of electrodes arranged on either side of the inlet hole in the flow path of the solution, and voltage monitoring apparatus for sensing fluctuations of voltage across the electrodes as particulates pass through the inlet hole for generating pulses representative of the size and count of the particulates passing through said inlet hole, the improvement comprising a passive screen having precision size openings, the screen being disposed between said electrodes and about the tube in the flow path of the solution prior to passage through the inlet hole, wherein said screen blocks particulates above a predetermined size from reaching the inlet hole without disturbing the electric field between electrodes and thereby the generation of pulses of the unscreened particulates.

2. The improvement according to claim 1, wherein the screen is supported on the tube.

3. The improvement according to claim 1 or 2, wherein the screen is spaced apart from the inlet hole.

4. The improvement according to claim 1, including a second particle counter apparatus substantially the same as the first, wherein the pump of the first particle counter apparatus communicates with the second, wherein the second particle counter apparatus has a screen having smaller openings than the screen of the first particle counter apparatus, and wherein the tube inlet hole of the second particle counter apparatus is smaller than the inlet hole of the first particle counter apparatus.

5. In a process for sizing and counting of particulate substances comprising the steps of:
 (a) suspending a particulate substance to be measured in an electrolytic solution;
 (b) drawing the solution through an inlet hole;
 (c) placing an electric field across a pair of electrodes on either side of said inlet hole while the solution is drawn therethrough; and
 (d) measuring the voltage across the inlet hole as the solution is drawn therethrough to obtain pulses representative of the size and count of the particulates passing through said inlet hole, the improvement comprising disposing a passive screen having precision size openings in the flow path of said solution between said electrodes and upstream of said inlet hole for blocking particulates above a predetermined size from reaching said inlet hole.

6. The process according to claim 5, comprising the further steps of:
 (a) drawing the solution sequentially through a second screen having precision size openings smaller than the preceeding filter or screen to block particulates above a predetermined size, and thereafter through a second inlet hole;
 (b) placing an electric field across the second inlet hole while the solution is drawn therethrough; and
 (c) measuring the voltage across the second inlet hole as the solution is drawn therethrough to obtain pulses representative of the size and count of the particulates present in the solution below the size blocked by the second screen.

* * * * *